US00PP09017P

United States Patent [19]

Olesen et al.

[11] Patent Number: Plant 9,017

[45] Date of Patent: Dec. 20, 1994

[54] MINIATURE ROSE PLANT NAMED POULMING

[75] Inventors: Mogens N. Olesen; Pernille Olesen, both of Fredensborg, Denmark

[73] Assignee: Bear Creek Gardens, Inc., Medford, Oreg.

[21] Appl. No.: 209,867

[22] Filed: Mar. 11, 1994

[51] Int. Cl.[5] ..... A01H 5/00

[52] U.S. Cl. ..... Plt./9

[58] Field of Search ..... Plt. 9, 7.1

*Primary Examiner*—Howard J. Locker

*Attorney, Agent, or Firm*—Klarquist Sparkman Campbell Leigh & Whinston

[57] ABSTRACT

A miniature rose plant, a mutation of the variety POU-Loral, having a distinctive light pink flower color as compared to the coral flower of its parent, while having similar plant habit, foliage and flower production.

1 Drawing Sheet

The present invention relates to a new and distinct variety of rose plant of the miniature class which was originated by us by selecting a pale pink flower color mutation from the coral flower colored variety POU-Loral (disclosed in copending application Ser. No. 08/209,844).

The primary objective of this selection was to produce a new rose variety having the same color of foliage, the same plant habit, and the same flower production of POULoral but with a distinctive and novel flower color. This objective was substantially achieved, along with other desirable improvements, as evidenced by the following unique combination of characteristics that are outstanding in the new variety and that distinguish it from its parents, as well as from all other varieties of which we are aware:

1. Similar plant growth habit, foliage and flower production to POULoral; and
2. Distinctive and novel flower color.

Asexual reproduction of this new variety by softwood cuttings as performed at Wasco and Somis, Calif. and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with the Royal Horticultural Society (London) Colour Chart, except where ordinary dictionary significance of color is indicated.

Classification:

*Botanical.*—*Rosa hybrida.*

*Commercial.*—Miniature.

FLOWER

Observations made from specimens grown in greenhouse environments at Somis and Wasco, Calif., and Fredensborg, Denmark.

Blooming habit: Recurrent.

Bud:

*Size.*—13 mm long when the petals start to unfurl.

*Form.*—The bud form is short, pointed ovoid.

*Color.*—When sepals first divide, bud color is Red Group 49B. When half blown, the upper and lower sides of the petals are Red Group 49C.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 144B. Shape: Funnel. Size: Small (6 mm by 3 mm). Surface: Smooth.

*Peduncle.*—Length: Short (38 mm to 44 mm). Surface: Smooth. Color: Medium green. Strength: Stiff, erect, slender.

Bloom:

*Size.*—Average open size is 38 mm. Singly, several together, in pyramidal to rounded clusters of 3 to 5 flowers.

*Stems.*—Short (13 to 15 cm); strong.

*Form.*—When first open: High centered. Permanence: Flattens, all petals curl, quill fashion.

*Petalage.*—Number of petals under normal conditions: 30 to 40.

*Color.*—The upper and reverse sides of the petals are Red Group 49C. The base of each petal has a small, Yellow Group 4C half-moon at the point of attachment. The major color on the upper side is Red Group 49C.

*Variegations.*—None.

*Discoloration.*—The general tonality at the end of the first and third days: No change. By the eighth day there is a gradual fading to Red Group 49D in open flowers.

*Fragrance.*—Slight.

Petals:

*Texture.*—Thin.

*Shape.*—Oval.

*Form.*—Tips slightly recurved, edges slightly quilled.

*Arrangement.*—Imbricated, with few, small petaloids in the center.

*Persistence.*—Drop off cleanly.

*Lastingness.*—On the plant: Very long (14 to 16 days). As a cut flower: Very long (10 to 12 days).

Reproductive parts:

*Anthers.*—Size: Small. Quantity: Few. Color: Yellow. Arrangement: Regular around styles, mixed with petaloids.

*Filaments.*—Color: White.

*Pollen.*—Color: Lemon yellow.

*Styles.*—Color: White.

*Stigmas.*—Color: Greenish white.

Form: Bush.

Growth: Vigorous, dwarf, upright, branching. Plant is 36 to 41 cm tall by 25 cm wide.

Foliage:

*Number of leaflets on normal mid-stem leaves.*—5.

*Size.*—Small (6 cm×4 cm).

*Quantity.*—Normal.

*Color.*—New foliage: Reddish green. Old foliage: Green Group 137A.

Leaflets:

*Shape.*—Pointed oval.

*Texture.*—Upper side: leathery, glossy.

*Edge.*—Serrated.

*Serration.*—Single, small.

*Petiole rachis.*—Color: Reddish.

*Petiole underside.*—Smooth, with a few glands.

*Stipules.*—Short, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Short (3 mm), straight.

*Color when young.*—Green and red.

Small prickles:

*Quantity.*—On main stalks: None. On laterals: None.

We claim:

1. A new and distinct variety of rose plant of the miniature class, a mutation of the variety POULoral, substantially as herein shown and described, characterized particularly as to novelty by the unique combination of its distinctive light pink flower color as compared to the coral flower of its parent, while having similar plant habit, foliage and flower production.

* * * * *

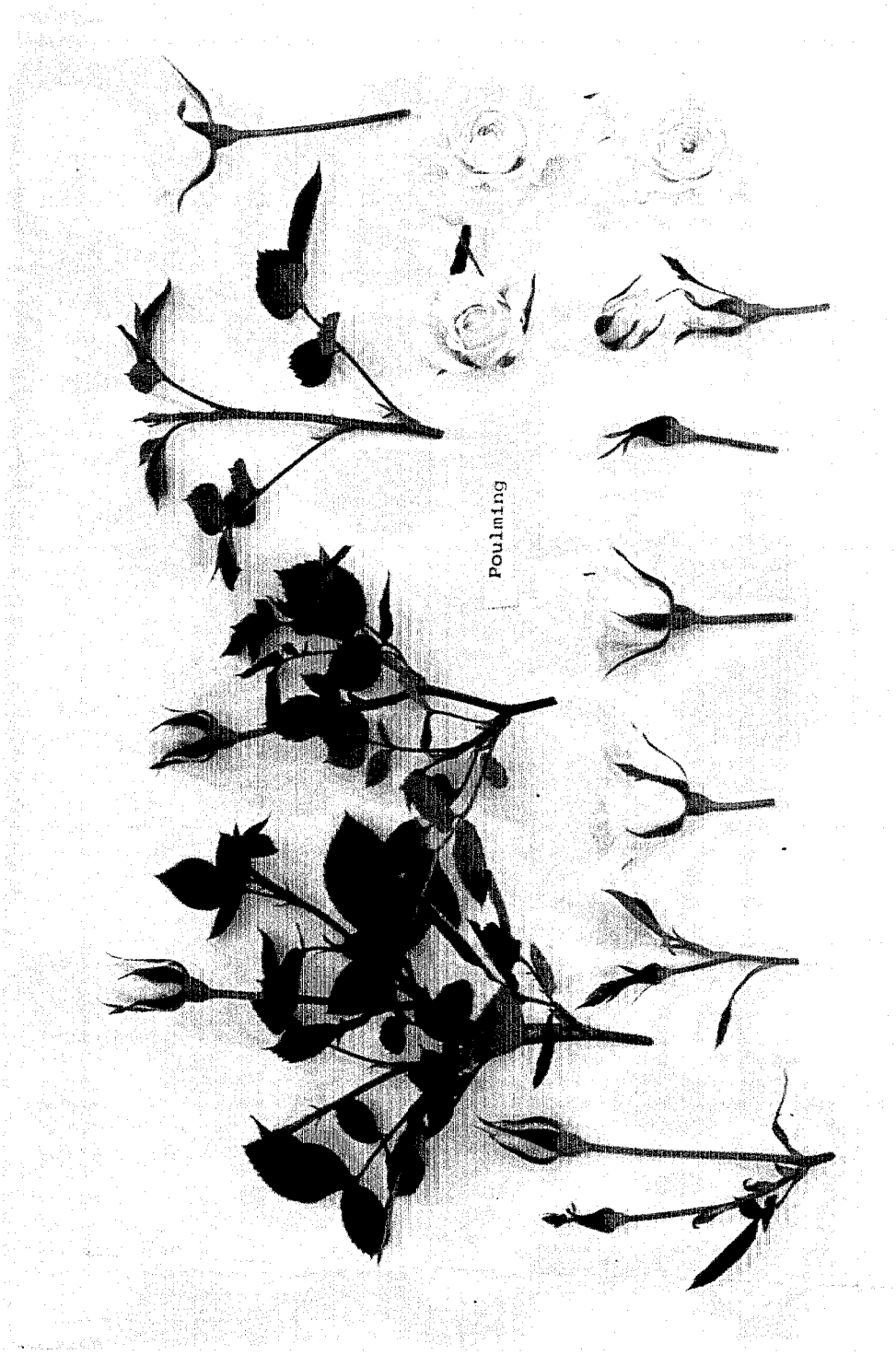
Poulming